United States Patent [19]

Tenerz et al.

[11] Patent Number: 4,941,473
[45] Date of Patent: Jul. 17, 1990

[54] GUIDE FOR MECHANICAL GUIDING OF A CATHETER IN CONNECTION WITH CARDIO AND VASCULAR EXAMINATION

[75] Inventors: Lars Tenerz, Upsala; Bertil Höök, Västerås; Thomas Engström, Upsala, all of Sweden

[73] Assignee: Radisensor AB, Upsala, Sweden

[21] Appl. No.: 297,256

[22] PCT Filed: Jul. 31, 1987

[86] PCT No.: PCT/SE87/00347
§ 371 Date: Jan. 11, 1989
§ 102(e) Date: Jan. 11, 1989

[87] PCT Pub. No.: WO88/00810
PCT Pub. Date: Feb. 11, 1988

[30] Foreign Application Priority Data

Aug. 4, 1986 [SE] Sweden .................... 8603304

[51] Int. Cl.⁵ .................................. A61B 5/00
[52] U.S. Cl. ........................... 128/637; 128/657; 128/667; 128/672; 128/772; 128/748

[58] Field of Search .......... 128/634, 637, 657, 667, 128/672, 673, 675, 748, 772; 73/705, 708, 715

[56] References Cited

U.S. PATENT DOCUMENTS

| 4,215,703 | 8/1980 | Willson | 128/772 |
| 4,274,423 | 6/1981 | Mizuno et al. | 128/675 |
| 4,329,980 | 5/1982 | Terada | 128/303.15 |
| 4,456,013 | 6/1984 | De Rossi et al. | 128/675 |
| 4,487,206 | 12/1984 | Aagard | 128/667 |
| 4,538,622 | 9/1985 | Samson et al. | 128/772 |
| 4,611,600 | 9/1986 | Cohen | 128/667 |

FOREIGN PATENT DOCUMENTS 8603956 7/1986 PCT Int'l Appl. .

Primary Examiner—Randall L. Green
Assistant Examiner—Randy Shay
Attorney, Agent, or Firm—Foley & Lardner, Schwartz, Jeffery, Schwaab, Mack, Blumenthal & Evans

[57] ABSTRACT

A guidewire for guiding a catheter is provided including a pressure sensor at the distal end of the guidewire and a ventilation passage for connecting the pressure sensor to ambient pressure.

26 Claims, 2 Drawing Sheets

GUIDE FOR MECHANICAL GUIDING OF A CATHETER IN CONNECTION WITH CARDIO AND VASCULAR EXAMINATION

BACKGROUND OF THE INVENTION

In radiographic examinations of the cardiac and vascular systems, catheters, i.e. thin plastic tubing, are utilised in several ways. Contrast liquid can be injected via the catheter for making parts of the vascular system visible on exposure to X-rays. Blood tests can be taken for analysis of dissolved gases, pH value, ion concentration etc. Hydrostatic pressure can be measured by a pressure transducer indicator connected to the catheter.

Catheters are not only used for diagnostic purposes, however. A new form of treatment of vascular constriction utilises catheters which are expandable by a heavy hydrostatic pressure being applied in a cavity, these being known as ballon catheters. In addition, pharmaceutical preparations can be injected through catheters for local drug administration.

For the end of the catheter to reach the desired place in the cardiac and vascular systems, a so-called guide wire is used, the latter being in the form of a wire with a dimension allowing its insertion into the catheter. Typical dimensions for catheters are: outside diameter 1–3 mm, inside diameter 0.5–1.5 mm, length 80–150 cm. The diameter of the guide wire may be about 0.5–1.0 mm. While the catheter is made from a polymer material, the guide wire is most usually made up from a metallic material, generally stainless steel.

In measuring pressure with known apparatus, the pressure is transmitted hydraulically in the catheter. This is problematical, due to the transmission properties of catheter/pressure transducer system. Furthermore, microscopic air bubbles can cause considerable deterioration in the transmission. This measurement is thus not reliable.

SUMMARY OF THE INVENTION

The present invention solves this and associated problems by the use of a miniaturised sensor placed near the distal end of the guide wire (the end nearest the sampling location), the signal transmission from the sensor taking place optically via an optical fibre built into the leader.

By the small dimensions enabled due to fibre-optic technology, the guide wire may be given such mechanical properties in the form of bending and torsional stiffness, and such formability as are required for its function of leading the catheter up to the sampling location in the cardiac and vascular systems. The optical signal transmission is not burdened with the deficiencies in transmission pertaining to the hydraulic principle.

Apart from more reliable diagnostic measuring values there is also obtained simpler handling. As a result of the extremely small dimensions of the pressure sensor and guide wire, pressure measurements can be made at points in the cardiac and vascular systems which have previously been inaccessible.

The distinguishing features characterizing the invention are apparent from the accompanying claims.

BRIEF DESCRIPTION OF THE DRAWINGS

A preferred embodiment of the invention will now be described with reference to the Figures, in which FIG. 1A is a cross-sectional view taken along lines A—A of FIG. 1.

DETAILED DESCRIPTION OF THE PREFERRED EMBODIMENTS

Figure 1:
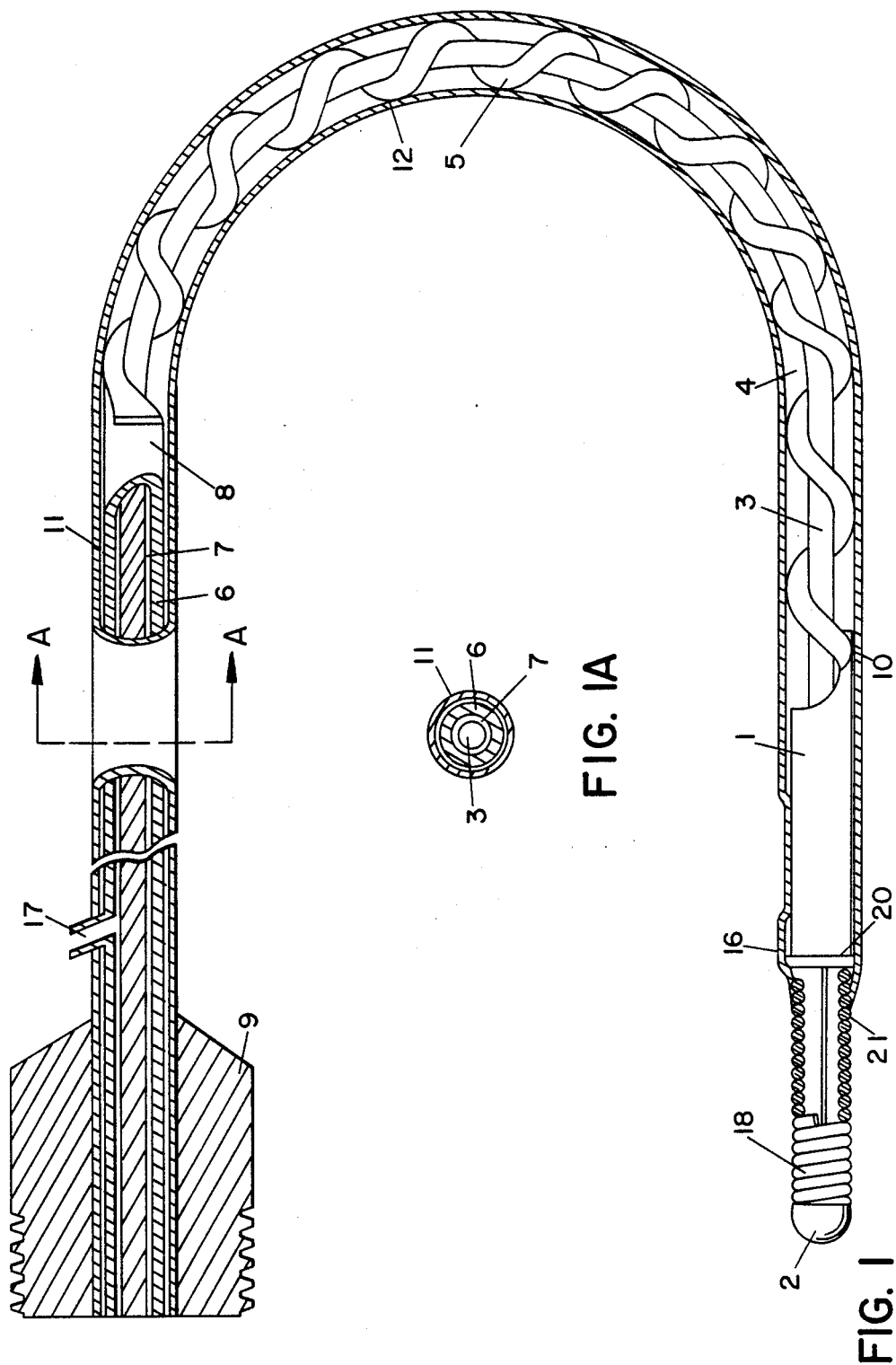
FIG. 1 illustrates a basic embodiment of the guide wire in accordance with the invention where certain portions have been broken away.

Turning now to FIG. 1, it will be seen that the pressure sensor 1 is placed close to the distal end 2 of the leader. Within the framework of what is possible to achieve using fibre-optical technology and micromechanics, a plurality of detailed embodiments of the sensor are conceivable, e.g. the one described in the Swedish patent application 8602836-2. The optical fibre 3 extends along the entire length of the guide wire and merges into a connection means 9 at the proximal end. Using the connection means, the fibre 3 can be connected with insignificant optical losses to another fibre or to an arrangement with a light source and a light detector. The pressure sensor 1 is mechanically connected, for example, by a welded joint 10 or by brazing to a sleeve 5, which comprises a helically wound metal wire in the depicted embodiment. In this region the guide wire will be easily flexible and resilient, which is necessary to avoid the risk for perforating vascular walls when the guide wire is inserted. The easily flexible part is usually 5–20 cm long and merges into a stiffer part towards its proximal end. The stiffer part may comprise a more tightly wound wire, or one that is thicker and thereby stiffer, or a thin-walled metal tube as illustrated in FIG. 1. The junction 8 between easily flexible and stiff portions can be abrupt or it can take place gradually. An advantage from the reliability and safety aspects is obtained when the parts 5 and 6 are fabricated from a single metal piece by mechanical processing, etching, shaping in some other way, etc. The distal end of the pressure sensor is connected to a further region of a helically shaped wire 18 with the aid of a welded joint 20 or by brazing. The sheath 5, 6 is surrounded by a thin-walled tube 12 of a polymer material (polyethylene, fluoropolymer, silicone rubber, fluoroelastomer, or polyurethane). The thin-walled tubing is shrunk over the helix in the joint area 21 between the pressure sensor 1 and the end portion by such as heating. This end portion will thus become even more flexible, which is necessary so that the guide wire does not cause damage to the sensitive tissues in the vascular system or the like. The guide wire should be treated with heparin to avoid the formation of blood dots. The distal end 2 of the guide wire is suitably rounded off and in the region of the pressure sensor the guide wire is provided with a sealing surface 16 for calibration purposes, (see Swedish patent SE-441 725).

A distinguishing feature characteristic for the guide wire and essential to its function is that there is a space 7 between the fibre 3 and the metal tube 6, this space constituting a ventilation duct for the pressure sensor 1. If the pressure sensor is adapted to record relative pressure variations, a reference pressure is namely required, which is suitably the prevailing air pressure. A ventilation passage is thus formed in the easily flexible part by the sleeve 5 being surrounded by the thin-walled tubing 12. The space 4 then constitutes a pressure connection extending from the pressure sensor via the space 7 and hole 17 out to the ambient atmosphere. It should be noted that the pressure transmission takes place via air which is in the guide wire, this giving a more reliable communication than if the transmission were to take place hydraulically, e.g. via water. The thin-walled tubing 12 is the material exposed to the body liquid. In order to improve biocompatibility of the material, i.e. its adaptivity to the biological medium, the polymeric material in the tubing can be coated with a thin film of a material having good tissue acceptance, e.g. heparin. In the stiff guide wire region the thin-walled tube may be replaced by a polymeric coating 11 optionally treated with heparin.

Figure 2:
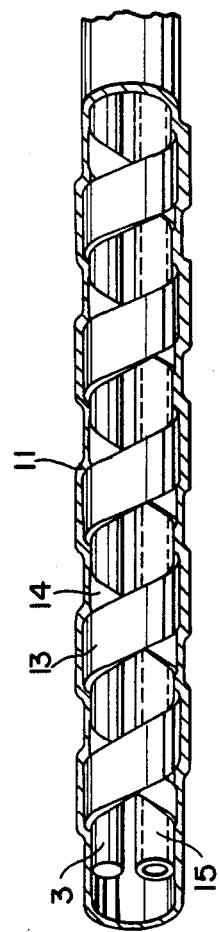
FIG. 2 is a detail of a special embodiment.

FIG. 2 illustrates an alternative detailed implementation of a short portion of the guide wire in accordance with the invention. The sleeve comprises two counter-wound metal bands 13, 14 in this case. This embodiment gives great torsional stiffness in combination with a relatively good ability to bend, which may be utilised to advantage in traversing the guide wire over vascular branches and sharp bends. In this case the ventilation passage consists of a thin capillary tube 15 extending parallel to the optical fibre 3.

The sheath 5, 6, 13, 14, fibre 3, tubing 12 or coating 11 suitably contain a compound, e.g. an oxide of some heavy metal, e.g. tungsten or bismuth to enable the guide wire to be visible in connection with radiography. The sheath 5, 6, 13, 14 may also be formed of an alloy, inter alia, of the metals iron, chromium and nickel, and at least one section of the sheath may be hardened.

One skilled in the art will understand that the invention can be modified in many ways within the scope of the accompanying claims.

We claim:

1. A guide wire having a distal end and proximal end for mechanically guiding a medical probe, comprising:
   (a) a miniaturized pressure sensor disposed at the distal end of the guide wire;
   (b) an air ventilation passage connecting the pressure sensor to a source of reference pressure;
   (c) a sheath formed of at least a first part adjacent the proximal end and a second part adjacent the pressure sensor, the sheath determining the torsional stiffness of the guide wire;
   (d) the first part being substantially inflexible and the second part being more flexible.

2. Guide wire as claimed in claim 1, wherein the sheath includes at least one section of elongated metal elements wound counter to each other for achieving a desired torsional stiffness.

3. Guide wire as claimed in claim 2, wherein the sheath includes in at least one section a metal tube in which an optical fibre is disposed.

4. Guide wire as claimed in claim 3, wherein the ventilation passage is formed by a space between the optical fibre and an inner wall of the metal tube.

5. Guide wire as claimed in claim 3, wherein an optical fibre extends in the guide wire and wherein the pressure signals from the sensor are transmitted optically by the optical fibre.

6. Guide wire as claimed in claim 1, wherein the sheath includes in at least one section a metal tube in which an optical fibre is disposed.

7. Guide wire as claimed in claim 6, wherein said ventilation passage is formed by a space between the optical fibre and an inner wall of the metal tube.

8. Guide wire as claimed in claim 6, further comprising at least one optical connection means placed at the proximal end of the guide wire, said connection means enabling the optical fibre to be connected with small light losses to another optical fibre.

9. Guide wire as claimed in claim 6, wherein at least a portion of the sheath is coated with at least one polymer.

10. Guide wire as claimed in claim 6, wherein at least a portion of the sheath is coated with at least one polymer.

11. Guide wire as claimed in claim 1, wherein the sheath contains a chemical compound containing an oxide of a metal.

12. The guide wire of claim 11, wherein said heavy metal is selected from the group consisting of bismuth and tungsten.

13. Guide wire as claimed in claim 1, wherein the sheath includes a tube, junction and spiral and is made from one piece of metal.

14. Guide wire as claimed in claim 1, wherein an optical fibre extends in the guide wire and wherein the pressure signals from the sensor are transmitted optically by the optical fibre.

15. Guide wire as claimed in claim 1, wherein the pressure sensor is mechanically connected to at least a portion of the sheath.

16. The guide wire of claim 15, wherein said pressure sensor is mechanically connected by brazing.

17. The guide wire of claim 15, wherein said pressure sensor is mechanically connected by welding.

18. Guide wire as claimed in claim 1, wherein a thin-walled tube is mounted on the sheath surface of the guide wire by shrinking.

19. Guide wire as claimed in claim 1, wherein the sheath is formed of an alloy of the metals iron, chromium and nickel, and at least one section of the sheath is hardened.

20. Guide wire as claimed in claim 1, wherein a thin-walled tube is mounted on the sheath surface of the guide wire by shrinking.

21. Guide wire as claimed in claim 1, wherein the sheath contains a chemical compound containing an oxide of a metal.

22. The guide wire according to claim 21, wherein said heavy metal is selected from the group consisting of bismuth and tungsten.

23. Guide wire as claimed in claim 1, wherein the sheath includes a tube, junction and spiral and is made from one piece of metal.

24. Guide wire as claimed in claim 1, wherein the sheath is formed of an alloy of the metals iron, chromium and nickel, and at least one section of the sheath is hardened.

25. The guide wire of claim 1 wherein the flexibility of the sheath changes abruptly at a juncture between the first and second parts.

26. The guide wire of claim 1 wherein the flexibility of the sheath increases gradually in the direction of the distal end in a region between the first and second parts.

* * * * *